United States Patent [19]
Berezin et al.

[11] Patent Number: 5,777,901
[45] Date of Patent: Jul. 7, 1998

[54] METHOD AND SYSTEM FOR AUTOMATED DIE YIELD PREDICTION IN SEMICONDUCTOR MANUFACTURING

[75] Inventors: Alan Berezin; Reuben Quintanilla, both of Austin, Tex.

[73] Assignee: Advanced Micro Devices, Inc., Sunnyvale, Calif.

[21] Appl. No.: 536,830

[22] Filed: Sep. 29, 1995

[51] Int. Cl.$^6$ .............................. G06G 7/48; G06F 15/00
[52] U.S. Cl. .................... 364/578; 395/500; 364/488; 364/489; 364/490; 364/491
[58] Field of Search ...................... 395/500, 916; 364/578, 488–491, 480, 579, 468.17, 237, 221.9, 468.28, 551.01; 371/27, 15.1, 16.1, 20.1, 21.1, 22.4, 22.1, 25.1, 26; 324/537; 356/237, 394

[56] References Cited

U.S. PATENT DOCUMENTS

| | | | |
|---|---|---|---|
| 3,751,647 | 8/1973 | Maeder et al. | 364/490 |
| 4,579,455 | 4/1986 | Levy et al. | 356/394 |
| 4,849,804 | 7/1989 | Mader | 257/798 |
| 5,274,434 | 12/1993 | Morioka et al. | 356/237 |
| 5,317,380 | 5/1994 | Allemand | 356/338 |
| 5,475,695 | 12/1995 | Caywood | 371/27.1 |
| 5,544,256 | 8/1996 | Brecher et al. | 382/149 |

OTHER PUBLICATIONS

A Wafer Scale fail Bit analysis System for VLSI Memory Yield Improvement, Sakai et al Proc. IEEE 1990 Int. Conference on Microelectronic Test Structures, vol. 3, Mar. 1990, 175–178.

Automatic In–Line Measurement for the Identification of Killer defects, Wilson et al, 1994 IEEE, pp. 5/1–5/8, Apr. 1994.

Automatic Defect Classification System for Patterned Semiconductor Wafers Breaux et al. [Jul. 1995] IEEE International Symposium on Semiconductor Manufacturing, 68–73.

Role of In–Line Defect Sampling Methodology in Yield Management, Nurani et al, Jul. 1995, International Symposium on Semiconductor Manufacturing, 243–247.

Automatic in–Line to end–of–line defect correlation using FSRAM test structure for quick killer defect identification, Wilson et al, 1994 IEEE, vol. 7, Mar. 94, 160–163.

A Spot–Defect to fault Collapsing Technique, Di et al, 1991 IEEE, pp. 580–583, Jun. 1991.

A fuzzy Logic Expert System for Automatic Defect Classification of Semiconductor Wafer defects, Laria et al, 1994 IEEE, pp. 2100–2106, Jun. 1991.

Simulating IC Reliability with Emphasis on Process–Flaw Related Earlyfailures Moosa et al, IEEE Transactions on Reliability, vol. 44, Nov. 4, 1995, 556–561.

*Primary Examiner*—Kevin J. Teska
*Assistant Examiner*—Herbert McNair
*Attorney, Agent, or Firm*—Merchant, Gould, Smith, Edell, Welter & Schmidt, P.A.

[57] ABSTRACT

Method and a system for performing die yield prediction in cooperation with wafer scanning tools. A program analyzes data associated with defects on a wafer substrate, the substrate including multiple layers and multiple die. Files are read that contain defect data for selected layers of the substrate. The defect data includes defect type and defect size information. The defect data is then stacked to identify the layer of first occurrence of each defect and the number, i.e., count, of layers upon which it was redetected. A kill factor is then assigned to each of the defects according to a set of rules, each such rule specifying defect parameters that include layer of first occurrence, redetect count, defect size, and defect type. Failure probabilities, indicative of yield, are then computed for the defects according to the assigned kill factors. The failure probabilites are utilized to calculate the estimated die loss for selected wafers by layer and defect type.

27 Claims, 11 Drawing Sheets

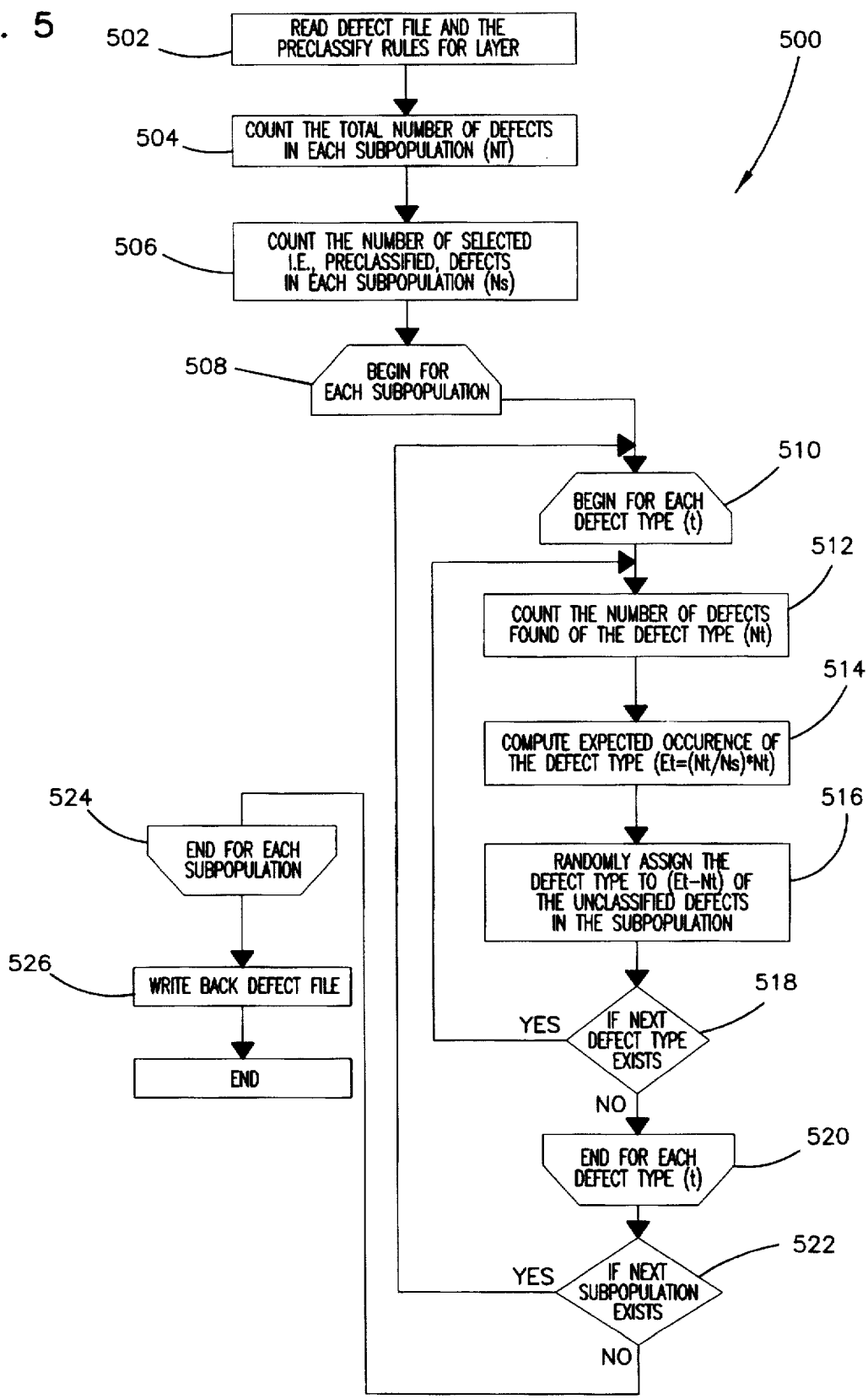

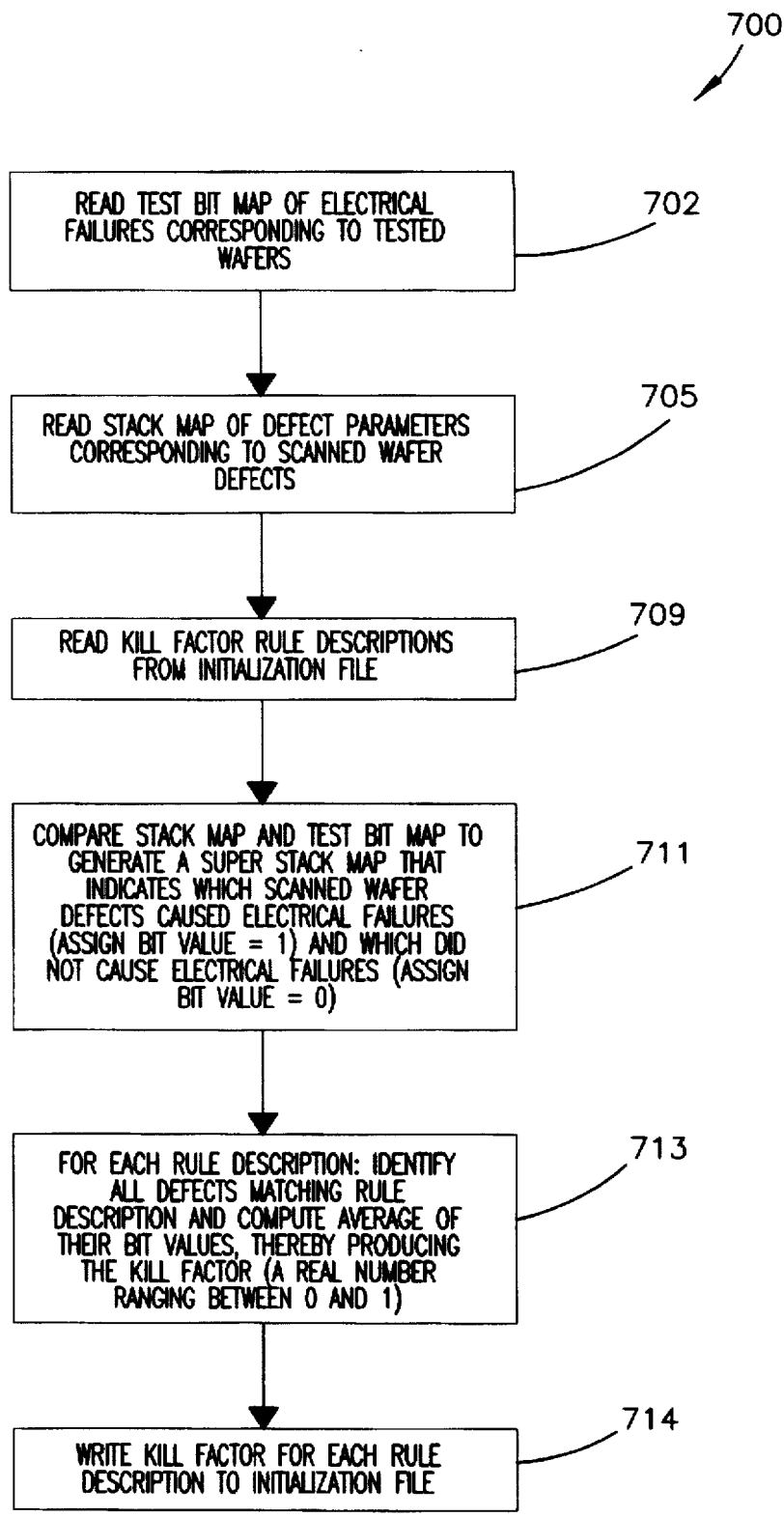

FIG. 8

Die Loss Output Format

| Lot # | Wafer # | Step ID | Result Time | DieLoss Total | DieLoss Type 0 | DieLoss Type 1 | DieLoss Type 4 |
|---|---|---|---|---|---|---|---|
| -- | -- | 1 | -- | $L_1$ | $L_{10}$ | $L_{11}$ | $L_{14}$ |
| -- | -- | 2 | -- | $L_2$ | $L_{20}$ | $L_{21}$ | $L_{24}$ |
| -- | -- | 3 | -- | $L_3$ | $L_{30}$ | $L_{31}$ | $L_{34}$ |
| -- | -- | 4 | -- | $L_4$ | $L_{40}$ | $L_{41}$ | $L_{44}$ |

METHOD AND SYSTEM FOR AUTOMATED DIE YIELD PREDICTION IN SEMICONDUCTOR MANUFACTURING

TECHNICAL FIELD

The invention relates generally to the manufacture of semiconductor integrated circuit ("IC") chips and, more particularly, to a method and system for performing in-line spacial map analysis of semiconductor wafer defects to predict die yield.

BACKGROUND OF THE INVENTION

Fabrication of semiconductor integrated circuits (ICs) is an extremely complex process that involves several hundred or more operations. They are fabricated by selectively implanting impurities into, and applying conductive and insulative layers onto, a semiconductor substrate. Semiconductor ICs (i.e., "chips") are not manufactured individually, but rather as an assembly of a hundred or more chips on a "wafer," which is then diced up to produce the individual chips.

Increasing production yield is an ongoing problem in the manufacture of semiconductor chips. Because of various defects that can occur in fabrication of a wafer, significant numbers of wafer die have to be discarded for one reason or another, thereby decreasing the percentage yield per wafer and driving up the cost of individual chips. Defects are typically caused by foreign particles, minute scratches and other imperfections introduced during photoresist, photomask and diffusion operations. Yield impacts the number of wafer starts at the inception of production needed to meet specific customer order quantities for finished chips at the end of the production line. With the high demand for semiconductor chips and more orders than can possibly be filled by a fabrication facility, predicting yield to accurately gauge wafer starts, and utilizing defect information to remove yield detracting operations, are important aspects of improving the efficiency, and hence output, of the fabrication facility.

Wafer scanning tools are utilized to identify defects that occur in the chip manufacturing process for the aforementioned purposes. Typically, such tools are located at a variety of positions along the production line and comprise automated-vision inspection stations for identifying visual irregularities in the wafer die as they move through the line. The irregularities, i.e., defects, are recorded according to their coordinates, estimate of size or other parameters and are stored as records in a database. The records represent raw information that must then be analyzed or otherwise processed off line to determine the impact, if any, of the identified defects on product yield. Some defects, for example, do not adversely affect yield as much as others, and therefore must be classified differently for analysis purposes.

Commercially available wafer scanning tools include those made by KLA Instruments Corporation of Santa Clara, Calif., Tencor Instruments Corporation of Mountain View, Calif., Inspex, Inc. of Billerica, Mass. and numerous other manufacturers. Despite significant advances made in wafer scanning technology, the various tools that are available suffer striking deficiencies. In particular, such tools lack the capability to perform certain advanced classification and analysis of defect information necessary to accurately determine the true impact of wafer defects on yield. While conventional tools offer simple data presentation capabilities, such as the display of wafer maps, histograms and charts, they do not adequately classify or process the defect data.

More specifically, a disadvantage suffered by scanning tools is that they do not adequately perform yield prediction operations beneficial in a manufacturing defect analysis, thereby limiting the utility thereof. For example, it is often desirable to further refine the defect data before manual inspection and classification of individual defects on the review station. Since each wafer can include so many defects it would not be practical to manually review and classify each of them, it would be desirable to utilize a method to randomly choose a statistically meaningful sample, i.e., subset, of such defects for consideration.

Historically, the review station operator randomly picks sets of defects that seem interesting and then reviews and classifies them. However, it is difficult for humans to systematically choose defects for this purpose that will be representative of all of the defects on the wafer. Some review stations are equipped with the ability to randomly move to different defects which the operator can then review and classify. A problem though with conventional randomizing methods performed on review stations is that they are not necessarily accurate in representing a true sampling of the wafer. For example, picking defects at random tends to result in the inordinate picking of defects that are part of a big cluster, because there are more of them, while defects of other types and in other locations on the wafer are overlooked. Therefore, it would be desirable to adopt an automated, consistent method for randomly identifying for review, i.e., "preclassifying," defects of interest. The methodology used to randomly identify, i.e., preclassify, defects preferably would focus on defect subpopulations defined in terms of defect size ranges, or alternatively in terms of locations on the wafer, so that the sample of defects chosen best reflects conditions actually occurring on the wafer.

Once defects of interest are randomly preclassified according to a beneficial methodology, they can then be manually reviewed and assigned appropriate classification codes by an operator to indicate defect type, e.g., big cluster, small cluster, or the like. Some equipment is available that automatically assigns such classification codes to defect types based upon machine visual attributes.

After defects are randomly chosen (i.e., preclassified), and then reviewed to assign classification codes thereto, the next task of interest is how to use the sample to estimate what the classification codes should be for the remaining defects on the wafer. The classification codes for the entire wafer should be extrapolated from the sample defect data consistent with the preclassification methodology used earlier to sample the subpopulations of defects. Finally, the estimated, i.e., extrapolated, defect data with classification code estimates for all defects, can be analyzed to provide warnings during manufacturing of certain adverse conditions.

Unfortunately, known defect analysis systems do not contemplate preclassification, review and extrapolation methodologies of the foregoing type for accurately and efficiently analyzing semiconductor defect data. Instead, known systems tend to rely simplistic, line of regression analyses, or other statistical correlations of defects to yield for a given lot or given wafer. More sophisticated systems are deficient in accounting for spacially inhomogeneous distributions of defect types and in extrapolating defect type information of the entire population from a small sample of reviewed defects.

Further, current yield prediction methodologies are inadequate in that they generate wafer or lot-based estimations of yield but do not accurately reflect estimations of yield for individual die. Prior methodologies tend to average the different effects of defects over a large number of die, making it difficult, if not impossible, to specifically review and locate the defects that kill a particular die. Thus they also do not allow for accurate detection of spacial patterns of defects on a wafer to determine what die locations are most effected by defect types.

Consequently, there is a need for a method and system that permits more accurate defect analysis to be performed in cooperation with semiconductor wafer scanning tools. More particularly, there is a need for a methodology and system that performs die level estimations of yield rather than wafer average, or lot average, systems based solely on n-variable linear regression or critical area calculations.

SUMMARY OF THE INVENTION

The present invention, accordingly, provides a method and a system for performing semiconductor manufacturing defect analysis in cooperation with wafer scanning tools that overcome or reduce disadvantages and limitations associated with prior methods and systems, particularly with respect to die yield prediction.

The present invention predicts yield at the die level in the semiconductor manufacturing process and enables the provision of warnings where, for example, die loss probability for particular defect types exceeds preselected parameters.

In one aspect the invention analyzes data associated with defects on a substrate, such as a semiconductor wafer, the substrate including multiple layers and multiple die. Files are read, each containing defect data for a selected layer of the substrate. The defect data includes defect type and defect size information. The defect data is then stacked to identify the layer of first occurrence of each defect and the number, i.e., count, of layers upon which it was redetected, with the defect data pertaining to occurrences on layers other than the layer of first occurrence then being discarded. A kill factor is then assigned to each of the defects according to a set of rules, each such rule specifying defect parameters that include layer of first occurrence, redetect count, defect size, and defect type. Failure probabilities, indicative of yield, are then computed for the defects according to the assigned kill factors.

The failure probabilites computed for the wafer defects are utilized to calculate the estimated total die loss ($DL_T$) for selected wafers. Other calculations performed include estimated die loss for individual layers of a wafer ($DL_L$) and estimated die loss for particular defect type ($DL_B$) of a wafer. The foregoing failure probabilities are presented in an output format that includes a header line for each lot followed by a line for each layer, with vertical columns pertaining to lot name, wafer, step identification, die loss for individual layers ($DL_L$), and defect types. The die loss output may be formatted as an ASCII file.

As an alternative form of presentation of die loss information, wafer maps are generated for selected layers of selected wafers showing die failure probabilities for individual die.

In another aspect, warnings are generated based upon the die loss information, to curtail yield detracting operations as they occur between fabrication steps.

In a preferred embodiment the invention is implemented as computer programs stored on computer-readable media. The programs are run on a system compatible with a commercially available wafer scanning tool or on the scanning tool itself.

A technical advantage achieved with the invention is the die level estimation of yield for any die on a wafer, as contrasted with yield estimation for the entire wafer or lot only. The present die level estimation enables identification of particular die that have failed or are expected to fail and enables detection of patterns on a wafer of failed die.

Another technical advantage achieved with the invention is that die failure probabilities, i.e., "kill factors," are expressed as a function of the number of times a defect is detected on different layers, thus being weighted based upon defect-by-defect stacking. Thus the system properly takes into account the known physical effect of defects that are caught multiple times.

Another technical advantage achieved is the provision of real-time analysis of estimated yield as compared with off-line analysis, thereby allowing faster response to fabrication problems at any given step in the manufacturing line.

BRIEF DESCRIPTION OF THE DRAWINGS

FIG. 5 is a process control flow diagram of the defect extrapolation functions performed by the yield predict program in step 404 of FIG. 4.

FIG. 7a is a process control flow diagram of the kill factor assignment functions performed by the yield predict program in step 408 of FIG. 4.

FIG. 7b is a schematic illustration of the comparison of stack map and test bit map memory structures as specified in FIG. 7a.

FIG. 8 is a table showing an example output format of die loss information generated by the system of FIG. 1.

DESCRIPTION OF THE PREFERRED EMBODIMENTS

Figure 1:
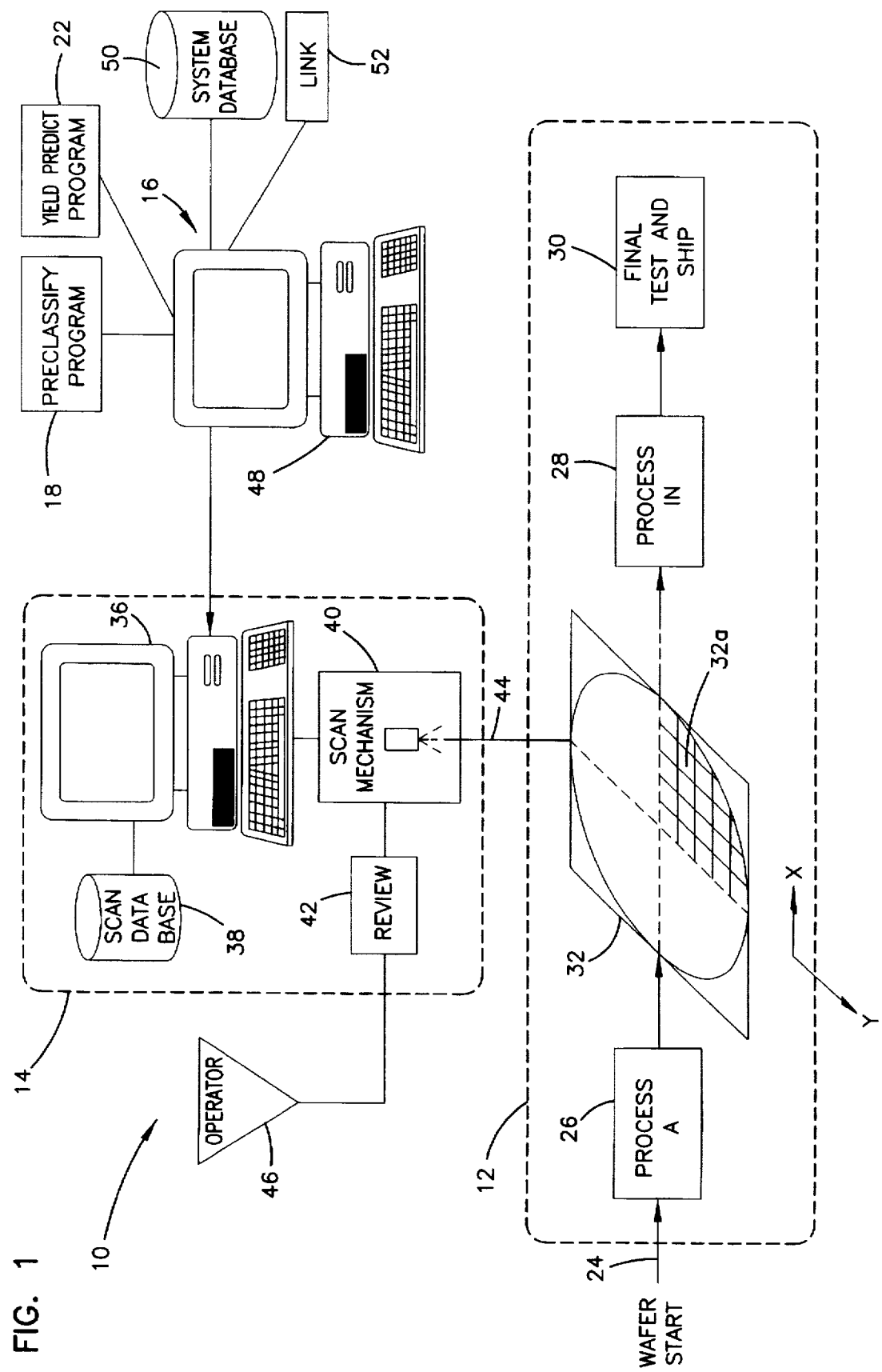
FIG. 1 is a schematic block diagram of a defect analysis system of the present invention for use with a wafer scanning tool in a semiconductor fabrication line to predict yield.

In FIG. 1, the reference numeral 10 refers to an environment that is a portion of a semiconductor wafer fabrication facility ("wafer fab") for practicing the preferred embodiment of the invention. The environment 10 includes a manufacturing line 12 for fabricating semiconductor integrated circuit (IC) products. A scan tool 14 is located at various stages of the line 12 for visually inspecting wafers comprising the ICs as they are being manufactured. A defect analysis system 16 is operatively coupled to the tool 14 for performing defect analysis operations of the preferred embodiment, as discussed more fully below.

Operatively coupled to the system 16 are several computer program utilities. Generally, a preclassify program 18 performs defect data classification functions in an early level of refinement of the defect data generated by the scan tool 14, for identifying statistically meaningful sets of sample defect data. The preclassified defect data is subsequently reviewed by an operator for purposes of assigning defect classification codes to the data. A yield predict analysis program 22 then extrapolates the defect data to estimate what the classification codes should be for the remaining, unclassified defects on the wafer, and then performs yield estimation operations to determine die loss probability for different defect types. The yield predict output is optionally used to produce warnings of when the die loss probability of a certain defect type for a given die exceeds a threshold value, for example, thereby indicating yield-detracting operations of the manufacturing process. The programs 18 and 22 are described fully below.

In the environment 10, semiconductor wafers are started in the manufacturing process, as indicated at line 24. The wafers are grouped and started in multiples, referred to as "lots", upon which a sequence of individual process operations are then performed. Process step A is first performed on a wafer lot as indicated by block 26. Subsequently, additional process steps are performed. Each process step, for example, comprises operations to be performed for a particular mask or layer of the wafers in the lot. Since the process steps are conventional and vary depending on the integrated circuit (IC) product being manufactured, they are not described in further detail. Block 28 represents completion of a sequence of many (up to N) processes, it being understood that in the typical wafer fab over one thousand processes, averaging up to a hundred or more steps each, must be completed. Upon completion, at block 30 the ICs comprising the wafers are ready for final test and shipment.

Following completion of Process A in block 26, the wafer scan tool 14 is used to perform a visual inspection of at least representative samples of the partially fabricated ICs in the wafer lot, as is represented by a wafer 32 located in proximity to the tool 14. While not shown, it is understood that similar inspections are performed at various stages of manufacturing of the wafer 32 and numerous tools 14 may be required to perform the inspections. Generally, the visual inspection performed by the scan tool 14 is used to identify defects of particular types to be used in an analysis of the effect of each defect type on the yield of the lot, or on the yield of individual wafers or wafer die in the lot. Engineering analysis of the process steps associated with particular defects may then be performed to identify and correct yield detracting operations.

The scan tool 14 comprises commercially available components and includes a computer 36, a database 38, a scan mechanism 40 and a review station 42. In a preferred embodiment, for example, the tool 14 is a KLA 21(xx) series defect scanning tool available from KLA Instruments Corporation. The scan mechanism 40 includes a microscope or other device for inspecting particles or other defects on the surface of the wafer 32. The wafer 32 may be moved relative to scan mechanism 40 by a transport mechanism (not shown) in the x and y directions perpendicular to the scan mechanism 40 to cause the microscope to sweep over the surface of the wafer in a series of adjacent, possibly overlapping, scan lines. Each wafer die, such as a die 32a, is scanned and the information derived therefrom is converted to digital form and processed by the computer 36. In operation the scan mechanism 40 compares one die of the wafer 32 to the next. Presumably, every die will be identical to the next and any differences indicate an error, i.e., a defect. As will be described further with reference to FIG. 2, the computer 36 constructs files comprising records of scanned defects that are then stored in the database 38. Each record includes information concerning the x-location and y-location of the defect, and an estimation of the x-size and y-size of the defect. Other fields of the records include, but are not necessarily limited to, classification codes for the defects.

The review station 42 is used by an operator 46 to manually study defects scanned by the mechanism 40. In a typical conventional application, the operator 46 must study the defects and either enter or modify classification codes into the stored records for the defects on the computer 36.

The tool 14 is capable of generating on its display various graphics indicative of scanned defects. These include histograms, wafer maps, charts or the like. The tool 14 is further capable of assembling files of defect records stored in the database 38 which may then be used to various perform defect analyses. As explained in detail below, the preclassify program 18 is utilized in cooperation with the tool 14 to modify defect records in improvement of subsequent analyses.

The defect analysis system 16 includes a computer 48, a system database 50 and a link 52. The link 52 operatively connects the system 16 to other control systems or computers (not shown) within the fab. In the preferred embodiment, the computer 48 is a commercially available PC or workstation running a Microsoft Windows operating system. Preferably, the system 16 is designed to read defect and sort files in the KLA Results File format, available from KLA instruments Corporation, and also the TLV format, available from Inspex, Inc. The programs 18 and 22 are stored in the system 16 as one or more programs for operation on the computer 48 and are preferably written in C++ programming language.

Figure 2:
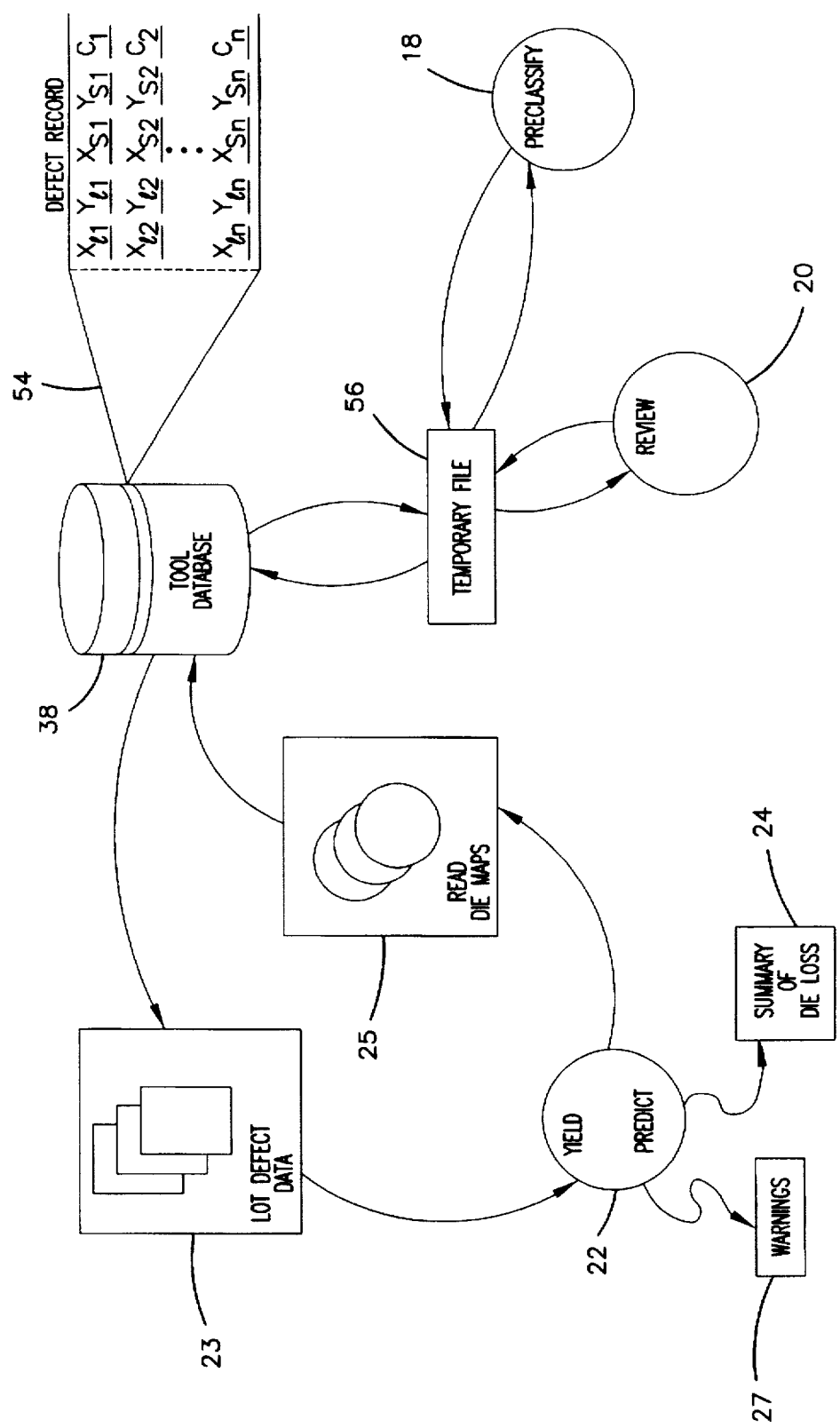
FIG. 2 is a conceptual block diagram of the sequence of operations performed on the defect data by the system of FIG. 1.

FIG. 2 illustrates a general process flow of the sequence of functions performed on defect data in the preferred embodiment of the invention. Referring to both FIGS. 1 and 2, the database 38 of the scan tool 14 is used to store wafer defect data in the form of "records." Shown schematically in FIG. 2 is the data structure of one such record 54 that contains data pertaining to the defects detected on the wafer 32. While not shown, it is understood that multiple records are stored in the database 38, each relating to wafer defects at different reticle layers of wafers in one or more lots. It is appreciated the records are organized into computer files by the computer 36 according to lot, layer and wafer designations, for example.

The record 54 comprises information concerning all of the defects (1 through n) detected on the wafer 32, including the x-location ($X_l$) and y-location ($Y_l$) of each defect, and an estimation of the x-size ($X_s$) and y-size ($Y_s$) of the defect. Another field of the record 54 is classification codes (C) for the defects. The classification codes indicate the nature of the defect and can be used to evaluate whether a defect is critical, i.e., whether it impacts the functionality of the IC. For example, classification codes might classify defects in terms of whether a defect is one that cuts a circuit line, or touches two lines, or whether it is above a particular layer or beneath a particular layer. The classification codes also might classify defects in terms of defect size, i.e., whether it is part of a big cluster or small cluster, or in terms of whether the defect is "discardable" in that it does not represent additional meaningful information for the defect analysis. Other criteria for classification codes are readily understood by those skilled in the art and therefore are not discussed further.

The classification codes for defects in the record 54 are used to make estimates concerning what impact, if any, a particular defect type will have on die or wafer yield. Once the wafer 32 is scanned and the defects are identified in the record 54 in terms of their location data $(X_l, Y_l)$ and size data $(X_s, Y_s)$, the normal procedure is then for an operator 46 to review the defects and manually enter the classification codes for each defect into the record 54. This is done by placing the wafer 32 on the review station 42 that includes a microscope (not shown) designed to automatically locate itself to the sites of the defects. The operator 46, based upon judgments about what the defect is, can classify it and then modify the record 54 to include the appropriate classification code.

Wafers can include hundreds of thousands of defects and it is a very time consuming task to manually enter classification codes for each of them in the record 54. Also, some defects do not contribute meaningfully to the data where they all relate to the same cluster of defects, such as scratch. Therefore, before manual review and classification of defects is performed by the operator 46, it is understood a decluster program (not shown), and/or the preclassify program 18, operate to automatically assign certain classification codes to selected defects in the record 54, as described below.

From the database 38, the computer 36 writes out a temporary file 56 that contains the records for a particular lot, such as a lot containing the wafer 32 and its corresponding record 54. The temporary file 56 is stored in the computer 48 of the analysis system 16.

If a decluster operation is performed on the data in the temporary file 56, a decluster program (not shown), running on the computer 48 or computer 36, reads the file 56 and declusters the defect data by entering classification codes into the record 54 to indicate a defect is either part of a cluster or is discardable. In particular, some defects are assigned a classification code indicating they are part of a cluster, i.e., defects in close proximity to one another on the wafer 32, and other defects of the same cluster are assigned a code that indicates them to be "discardable." The discardable defects therefore can be removed from consideration in later classification and yield determining procedures. This procedure is referred to as "declustering" the defect data. The decluster program is implemented using any available decluster algorithm and therefore will not be described in further detail.

Once the decluster operation is performed, or instead of the decluster operation being performed, the preclassify program 18 reads the file 56 and further refines the defect data by changing classification codes in the defect records to indicate a random sample of defects which are to be reviewed at the review station 42. The random sample is chosen according to a set of randomizing rules in which defects are chosen from defined subpopulations of defect data, as will be described below. At the review station 42 the chosen sample of defects is classified by defect type. In this manner, a subset of defect records is created that may be used to extrapolate the defect types for all of the defects on the wafer 32.

The details of how the preclassify program 18 determines which defects are to form the preclassify sample are described fully below. The preclassify program 18 may be implemented by, for example, activating a command on the computer 48 whereupon the preclassification functions are then automatically applied to the defect data. It is understood that the preclassify program 18 is transportable across all scan tools 14 that provide defect coordinates with defect size. Further, it is understood the preclassify program 18 may be implemented with or without having first declustered the defect data.

After the preclassify program 18 completes its operations, the computer 36 of the scan tool 14 reads the temporary file 56 so that at the review station 42, only the defects that were identified as preclassify defects will show up for review. Icon 20 (FIG. 2) indicates the performance of such a review on the review station 42 following refinement of the data by the preclassify program 18. The operator 46 performs the manual review of the wafer and enters defect type classification codes for the identified sample of defects. Since the sample of defects is relatively small compared to all of the defects on the wafer, e.g., approximately 50 defects, the manual review and classification procedure is not overly burdensome. It is understood that the manual review alternatively can be performed automatically, with appropriate machine vision processing equipment.

With the classification codes thus "re-coded" by the operator 46 on the review station 42, the modified file 56 may then be acted upon by the yield predict program 22. As will be explained fully below, the yield predict program 22 includes a module that first reads a lot defect data file 23 indicative of the re-coded defects for the layers, and retrieves the preclassify rules for the particular layer of defects being considered. Using this information, the program 22 includes a module that estimates what the classification codes should be for the remaining, unclassified defects on the wafer, extrapolated from the small number of already classified defects. The program 22 then stacks all layers for each wafer of a fabrication lot to determine the layer of first occurence and number of layers detected for each defect, assigns failure, i.e., "kill" factors to each defect on each wafer, and then computes the net failure probability for each die of each wafer. A summary 24 of die loss by layer and by defect type may then be generated. Optionally, data returned to the database 38 may be used to generate maps of each wafer for each layer showing die failure probabilities. The generation of such maps is schematically illustrated by dead die map data block 25, it being understood the maps are typically produced using the scan tool's existing software from a KLA results file, for example, modified by the yield predict program 22.

The yield predict program 22 may further includes logic for producing warnings 27 on a display to indicate the existence of inordinate die loss probabilities for particular defect types, as determined from the yield predict analysis. The display is understood to be either the display of the system 16, the display on the tool 14, or some other display.

Figure 3:
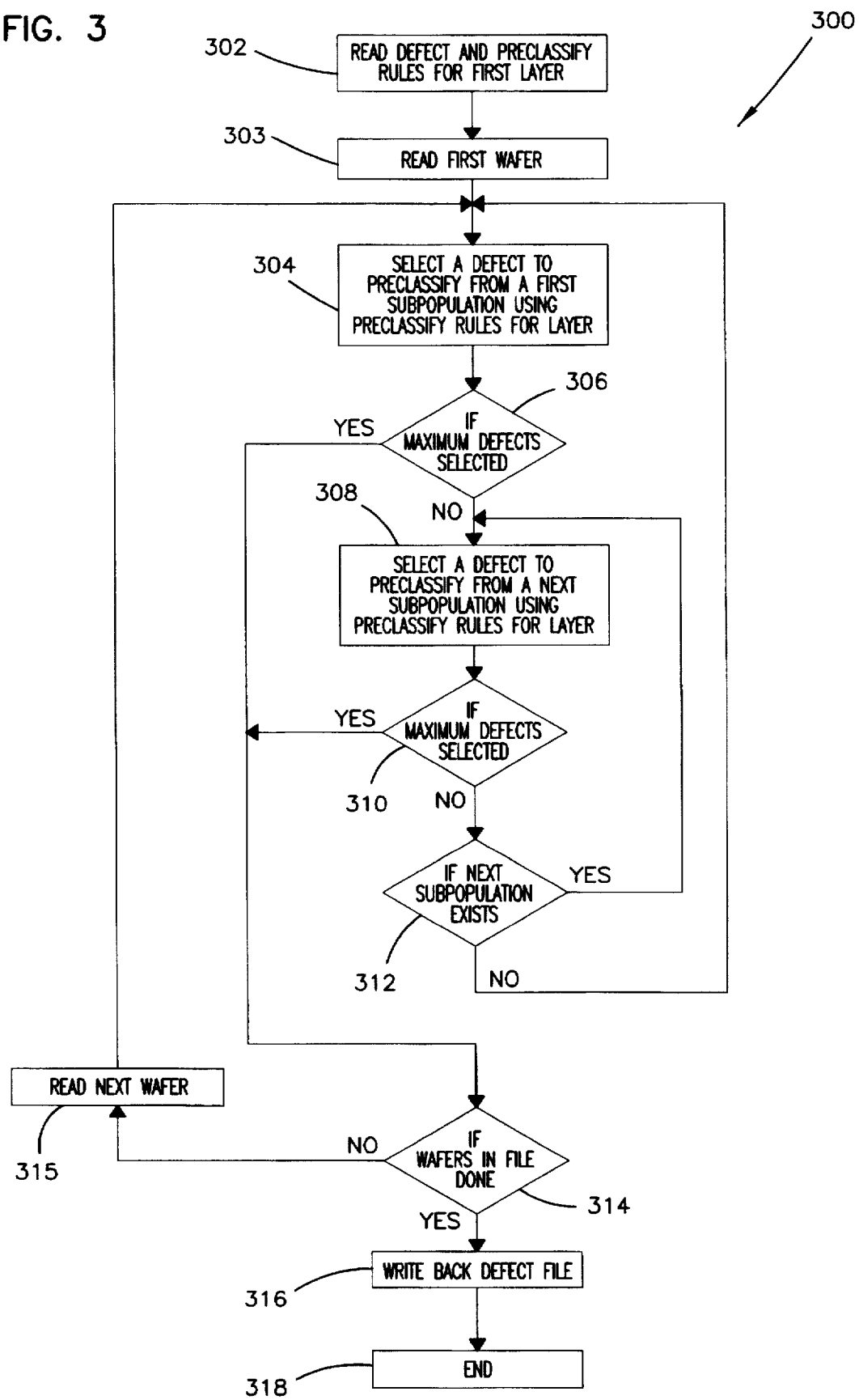
FIG. 3 is a process control flow diagram of the preclassify program of the system of FIG. 1.

FIG. 3 is a process control flow diagram 300 of the preclassify program 18. The preclassify functions performed by the program 18 are run on a defect lot file such as the temporary file 56. The functions are specific to each production layer and are separately performed for all layers of interest.

Preclassify rules, as described below, are predefined for each layer and then automatically applied when the program 18 is executed to preclassify defects for that layer of the lot file. A layer identifier in the file 56 indicates the particular layer and hence the particular preclassify rules to be executed for that layer. Execution of the program 18 occurs independently for each layer of interest until execution for all layers have been completed.

In step 302 a defect file containing defect records for a fabrication layer of interest of a wafer lot is read into the computer 48 of the system 16. Similarly, an initialization file is read that contains preclassify rules, i.e., parameters, for the layer of interest.

It is understood that prior to execution of the preclassify program 18, the preclassify rules, i.e., parameters, to be applied for each layer of interest are defined. The following parameters are initially set up for each layer: (1) the total number of defects to be reviewed, i.e., preclassified; (2) the code with which chosen defects are to be classified; (3) the defect type(s) which may be chosen; (4) the subpopulations (e.g., defect size ranges or defect locations) in which defects are to be randomly chosen; and (5) the randomizing function to be used to randomly choose defects within the subpopulations.

In the preferred embodiment, an initialization file is written for each lot defect layer specifying the foregoing parameters. Shown below is an example initialization file \DKT.INI illustrating the syntax of the preferred embodiment, with characters to the right of an asterisk ("*") being read as comments.

\DKT.INI *

| | |
|---|---|
| BeginClassifyScheme | *This token begins the syntax of the rules |
| MaxDefects=30% | *Preclassify 30% of all defects |
| MaxDefects=50 | *But only up to a max of 50 defects |
| PreClassifyCode=255 | *Change defect type code to 255 for *preclassified defects |
| PreClassify Type=0, 34 | *Only choose from among defect types *0 or 34 |
| RandomDie=[2, 4] | *The first subpopulation is 2–4um sized *defects. Use the RandomDie *randomization function to choose defects *in this subpopulation |
| RandomDie=[4, 6] | *The second subpopulation is 4–6um sized *defects. Use the RandomDie *randomization function to choose defects *in this subpopulation |
| RandomDefect=[6, *] | *The third subpopulation is 6um and *greater sized defects. Use the *RandomDefect randomization function to *choose defects in this subpopulation |
| EndClassify Scheme | *This ends the rules |
| * | |

The number of defects to be chosen (MaxDefects) can be expressed as a total number, a percentage of defects on a wafer, or a combination thereof. Any number can be chosen so long as it represents a statistically meaningful sample of defects. The preclassify types ("PreClassifyType") from which defects can be selected are defects that have not been classified at all ("0") or small clusters ("34") in the present embodiment, although any number or any type of defect may be specified as a preclassify type. Three subpopulations ("|2, 4|", "|4, 6|" and "|6, *|") are specified above. The subpopulations represent three different defect size ranges, although it is understood that any number of subpopulations of different defect size ranges are contemplated. Further, the subpopulations can alternatively define, instead of size ranges, defect locations expressed, for example, as boxes, quadrants, radial zones or the like.

The choice of the randomizing function ("RandomDie" or "RandomDefect") determines how the defects are randomly chosen from all of the defects in the subpopulation. The RandomDefect function means to randomly select any defect in the subpopulation. In contrast, the RandomDie function means to first select a die at random from amongst all die that have a defect or defects that are in the subpopulation, and then to select a defect at random from within that selected die. The advantage of using the RandomDie function is that it offers a better chance of selecting meaningful defects that might exist in less populated die, as opposed to statistically concentrating on defects in areas of high defect density.

In step 303 the defect records for a first wafer, pertaining to the layer of interest, are read. In step 304 a defect is selected from the records and given a "preclassify" code. The defect is selected from the first subpopulation defined by the preclassify rules. The manner in which the defect is selected depends upon the randomizing function specified in the rules for that subpopulation. For example, if the RandomDefect function is specified, the defect is randomly selected from all of the defects in the subpopulation that meet the specified preclassify type. If instead the RandomDie function is specified, the defect is randomly chosen by first randomly selecting a die within the subpopulation that includes at least one defect of the specified preclassify type, and then from the selected die, selecting a defect of the specified preclassify type.

It is understood that if in step 304 no defect can be selected because there are no defects in the subpopulation that meet the specified preclassify type, then execution proceeds to the next step without making a selection.

In step 306 a decision is made whether the maximum number of defects specified in the preclassify rules have already been selected. If so, execution proceeds to step 314 where the defect file is written back to its source. If in step 306 the maximum number of defects has not been selected, execution continues to step 308. As indicated above, the maximum number of defects can be expressed as a number or a percentage of defects on a wafer and the only requirement is that it represent a statistically meaningful sample.

In step 308 a defect is selected and preclassified, taken from the next subpopulation defined by the preclassify rules. The manner in which the defect is selected depends upon the randomizing function specified in the rules for that subpopulation, as described above.

In step 310 a decision is made whether the maximum number of defects have been selected yet, and if so, execution proceeds to step 314. If the maximum number have not been selected, in step 312 a decision is made whether a next subpopulation exists, as defined in the preclassify rules. If so, execution returns to step 308 and the process of selecting and preclassifying is repeated for that subpopulation. If in step 312 there is no next subpopulation defined in the preclassify rules, execution returns to step 304 and the process of selecting and preclassifying begins again with the first subpopulation.

The processing loops of step 312 thus repeat until the maximum number of defects have been selected by the preclassify program 20. In step 314 a determination is made whether all of the wafers in the defect file have been processed. If not, in step 315 the next wafer is read and execution returns to step 304. If in step 314 all of the wafers have been considered, in step 316 the defect file is written back to a specified memory location. In step 318 execution ends. It is understood the process may be repeated for different layers according to the preclassify rules for that layer.

Figure 4:
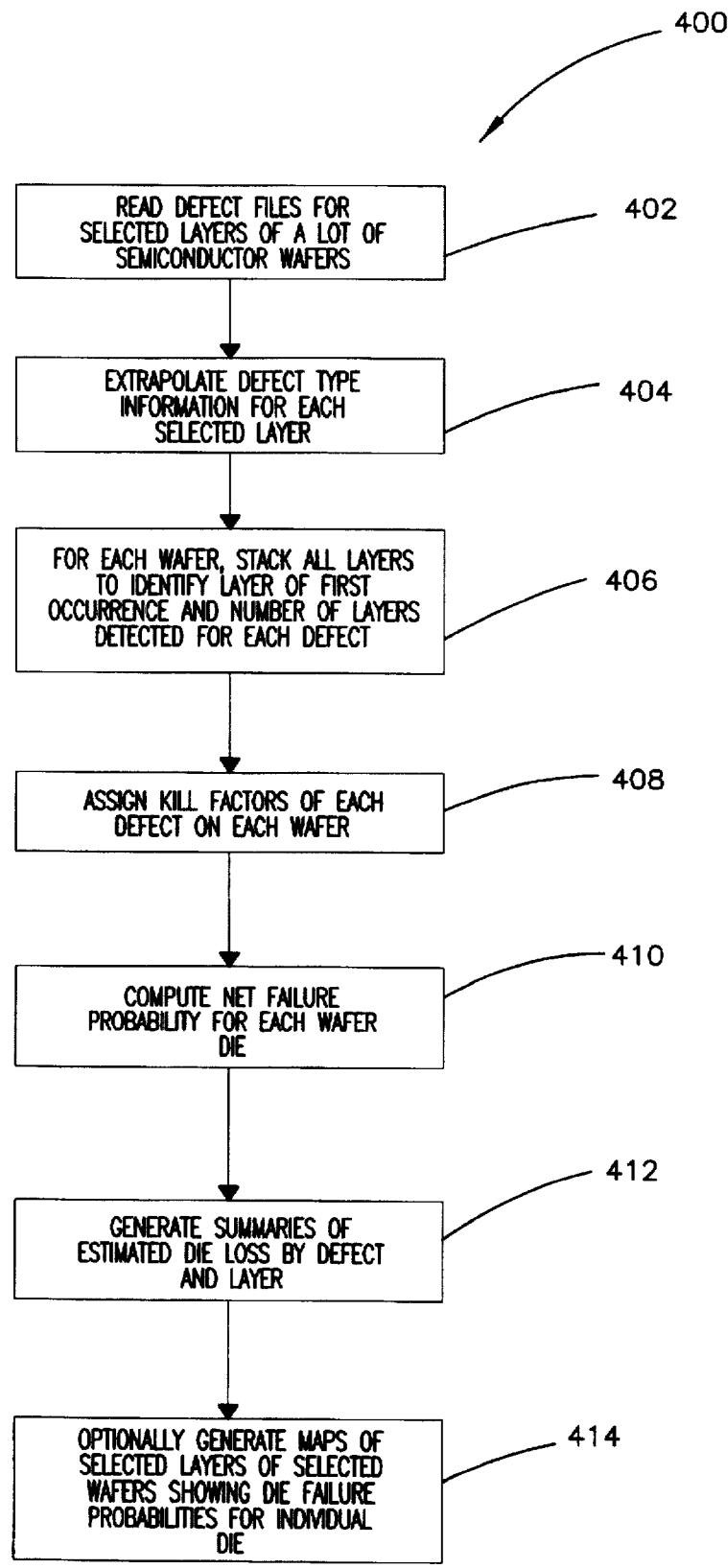
FIG. 4 is a process control flow diagram of the yield predict program of the system of FIG. 1.

FIG. 4 is a general process control flow diagram 400 of the yield predict program 22. In step 402 the program 22 first reads lot defect data files for selected fabrication layers of the semiconductor wafers comprising the lot. The files include information indicative of the re-coded defects for the layers, as performed by the preclassify program 18. The program 22 further retrieves the preclassify rules for the particular layer of defects being considered, for use in extrapolating the data in step 404. In step 404, the program 22 includes a module that estimates what the classification codes should be for the remaining, unclassified defects on each wafer, extrapolated from the small number of already classified defects. This process is subsequently described with reference to FIG. 5.

In step 406 the program 22 then stacks all layers for each wafer of a fabrication lot to identify the layer of first occurrence of each defect and number of layers upon which each defect is detected. This process is subsequently described with reference to FIGS. 6a and 6b.

In step 408 failure, i.e., "kill" factors are assigned to each defect on each wafer. This process is subsequently described with reference to Table II below.

In step 410 the net failure probability is computed for each wafer die, as explained more fully below.

In step 412 a summary of estimated die loss output is generated, as explained below with reference to FIG. 8.

In step 414, maps are optionally generated of each wafer for each layer showing die loss. The generation of such maps is explained further below with reference to FIG. 9.

FIG. 5 is a process control flow diagram 500 of the defect extrapolation step 404 of FIG. 4. The defect extrapolation functions performed by this module of the program 22 are run on a defect lot file such as the temporary file 56. The functions are specific to each production layer and are separately performed for all layers of interest.

In step 502 a defect file containing defect records for a fabrication layer of interest of a wafer lot is read into the computer 48 of the system 16. Similarly, an initialization file is read that contains preclassify rules, i.e., parameters, for the layer of interest. The preclassify rules are the same rules used for the layer in performing the preclassify function as described with reference to FIG. 3.

The remaining steps of the diagram 500 are best understood with reference to the extrapolation example of Table I set forth below.

In step 508 a processing loop begins that, as explained more fully below, is executed for each subpopulation and for each defect type (t) identified from the selected defects ($N^S$) in each subpopulation. The processing loop of steps 508–524 randomly assigns the classification codes for the defect types to unselected defects in the subpopulations so that the number of classified defects for each defect type in each subpopulation is approximately equal to the expected occurrence for that defect type in that subpopulation. The result is that from the small sample of selected defects of different defect types in each subpopulation, the proper classification codes for all defects in the subpopulations are extrapolated and assigned, thereby representing the true number of defects of each defect type in each subpopulation.

In step 510 a processing loop begins for each defect type (t) in the subpopulation, as explained more fully below. It is understood the different defect types (t) for which the loop of steps 510–520 are applied were previously determined by review of the selected defects ($N^S$) by the operator 46. Specifically, as described previously with reference to FIG. 2, after the sample of defects were selected, i.e., preclassified, using the preclassify program 18, the selected defects were reviewed on the review station 42 and assigned the appropriate classification code for that defect type.

Table I, for example, illustrates three different defect types t1, t2, and t3 that were identified during such a manual review on the review station 42. In the example, 20 defects were selected ($N^S$=20) for review out of a total of 100 existing defects ($N^T$=100). When the defects to be reviewed are randomly selected according to the preclassify rules from the three subpopulations A, B and C, the defect types are found in different proportions in each of the subpopulations, thereby accurately reflecting the number of different defect types for different defect size ranges on the layer. For example, in subpopulation A (defects in a size range of 0 to 2 um), the number of selected defects of each

TABLE I

Extrapolation Example

| | Subpopulation A [0, 2] | Subpopulation B [2, 5] | Subpopulation C [5, *] |
|---|---|---|---|
| Number Defects Total ($N^T$) = 100 | $N^T_A$ = 50 | $N^T_B$ = 40 | $N^T_C$ = 10 |
| Number Defects Selected ($N^S$) = 20 (Max = 20%) | $N^S_A$ = 8 | $N^S_B$ = 7 | $N^S_C$ = 7 |

| | # Found | # Expected | # Found | # Expected | # Found | # Expected |
|---|---|---|---|---|---|---|
| Defect Type 1 | $N_{At1}$ = 2 | $E_{A1}$ = 12.5 | $N_{Bt1}$ = 5 | $E_{B1}$ = 28.5 | $N_{Ct1}$ = 7 | $E_{C1}$ = 10 |
| Defect Type 2 | $N_{At2}$ = 4 | $E_{A2}$ = 25 | $N_{Bt2}$ = 2 | $E_{B2}$ = 11.5 | $N_{Ct2}$ = 2 | $E_{C2}$ = 0 |
| Defect Type 3 | $N_{At3}$ = 2 | $E_{A3}$ = 12.5 | $N_{Bt3}$ = 0 | $E_{B3}$ = 0 | $N_{Ct3}$ = 2 | $E_{C3}$ = 0 |
| | $N^T_A$ = 50 | | $N^T_B$ = 40 | | $N^T_C$ = 10 | |

In step 504 of FIG. 5, a count is made of the total number of defects ($N^T$) in each defect subpopulation defined by the preclassify rules. In the present example of Table I, there are three subpopulations A, B, and C that define defect size ranges of [0, 2], [2, 5], and [5, *], respectively. The total number of defects ($N^T$) counted in each of the subpopulations A, B, and C are indicated as $N^T_A$=50, $N^T_B$=40, and $N^T_C$=10, respectively. In step 506 a count is made of the number of selected, i.e., preclassified, defects in each subpopulation. In Table I the number of selected defects in each of the subpopulations A, B, and C are $N^S_C$=8, $N^S_B$=7, and $N^S_B$=7, respectively.

type out of the 20 defects reviewed are $N_{At1}$=2, $N_{At2}$=4, and $N_{At3}$=2. It is understood that had the defects been chosen at random on the wafer without being chosen from different subpopulations, the relative proportions of defect types would likely be very different and less accurate.

Referring to the processing loop of steps 510–520, it is understood that execution begins with a first defect type (t) identified in a first subpopulation of the loop beginning at step 508. In step 512, a count is made of the number of defects found in the subpopulation of the defect type ($N_t$). In Table I, for example, the count of defects of type t1 in subpopulation A is equal to 2, i.e, $N_{At1}$=2. In step 514 the expected occurrence of the defect type is computed. The expected occurrence is an extrapolation from the number of defects actually found of the defect type ($N_t$), to a number of how many should be expected for that type in the entire subpopulation. The expected occurrence ($E_t$) is determined by dividing the number of the defect type found ($N_t$) in the subpopulation by the number selected for review ($N^S$) in the subpopulation, and then multiplying that amount by the total number of defects ($N^T$) in the subpopulation (i.e., $E_t=(N_t/N^S)*N^T$). In Table I, the expected occurrence for defect type t1 for subpopulation A is calculated as follows: $E_{At1}=((N_{At1}/N^S_A)*N^T_A)=(\frac{2}{8})*50)=12.5$.

In step 516 the defect type is randomly assigned to unclassified defects in the subpopulation so that the total number of classified defects of the defect type in the subpopulation approximately equals the expected occurrence ($E_t$) for that defect just calculated in step 514. Since the defects found in the subpopulation ($N_t$) already have been classified, this amount is subtracted from the expected occurrence to equal the number of unclassified defects that need to be classified. Therefore, the number of unclassified defects that needs to be randomly classified as defect type (t) is equal to $E_t-N_t$. In Table I, the number of defects to be randomly classified in subpopulation A is equal to $E_{At1}-N^T_A=12.5-2=10.5$. Since 10.5 is not a whole number, but a statistical representation, the number actually classified will be rounded up or down.

In step 518 a determination is made whether a next defect type exists in the subpopulation. If so, execution returns to step 512 and the process loop is repeated. Otherwise execution proceeds to step 520 where the process loop begun in step 510 ends. In the example of Table I, it is understood the process loop of step 510 would be repeated for each of the three defect types t1, t2 and t3.

In step 522 a determination is made whether a next subpopulation exists and if so, execution returns to step 510. If no next subpopulation exists, execution proceeds to step 524 where the process loop begun in step 508 ends. In the example of Table I it is understood the process loop of step 508 would be repeated for each of the three subpopulations A, B, C.

As a result of the foregoing, the defect records of the layer defect file have been updated so that all of the defects have classification codes assigned to them. The classification codes were extrapolated, for each defect in each subpopulation, from the smaller number of sample defects originally reviewed and classified by the operator 46 at the review station 42. The extrapolated defect data represents the best estimation of defect types on the layer because the data takes into account samples of defects in different subpopulations of the layer, particularly different defect size ranges as determined by the original preclassify rules. Of course, other subpopulation criteria may be utilized, including subpopulations that define defect locations expressed as boxes, quadrants, radial zones or the like.

In step 526 the file with the extrapolated defect data is written back to a storage location, such as the scan database 38. Execution ends in step 528.

Figure 6A:
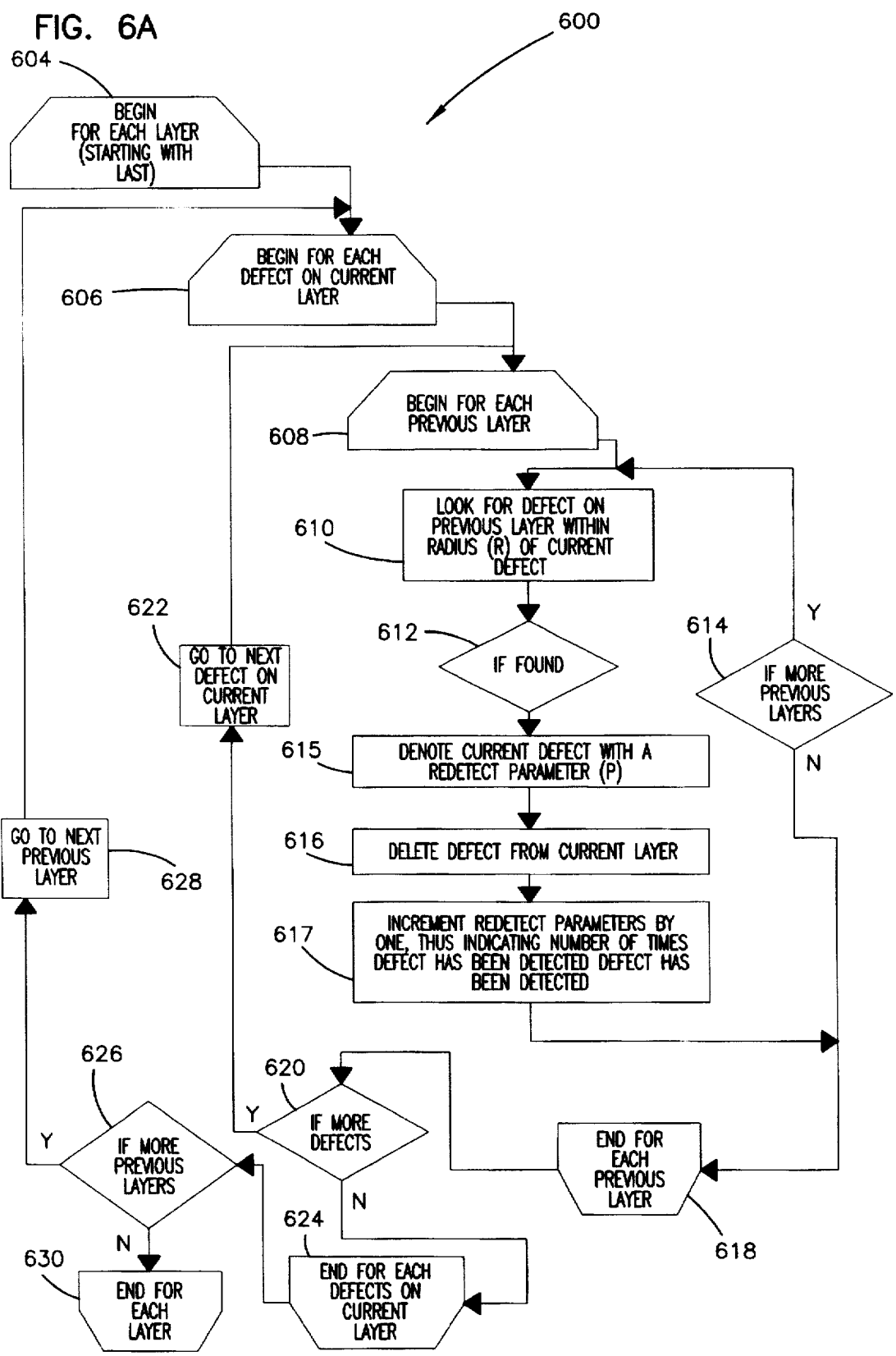
FIG. 6a is a process control flow diagram of the layer stacking functions performed by the yield predict program in step 406 of FIG. 4.

FIG. 6a is a process control flow diagram 600 illustrating details of the layer stacking step 406 of FIG. 4. The layer stacking functions performed by this step of the program 22 are run on a defect lot file such as the temporary file 56, after its defect data is refined by the extrapolation function described above with reference to FIG. 5.

Figure 6B:
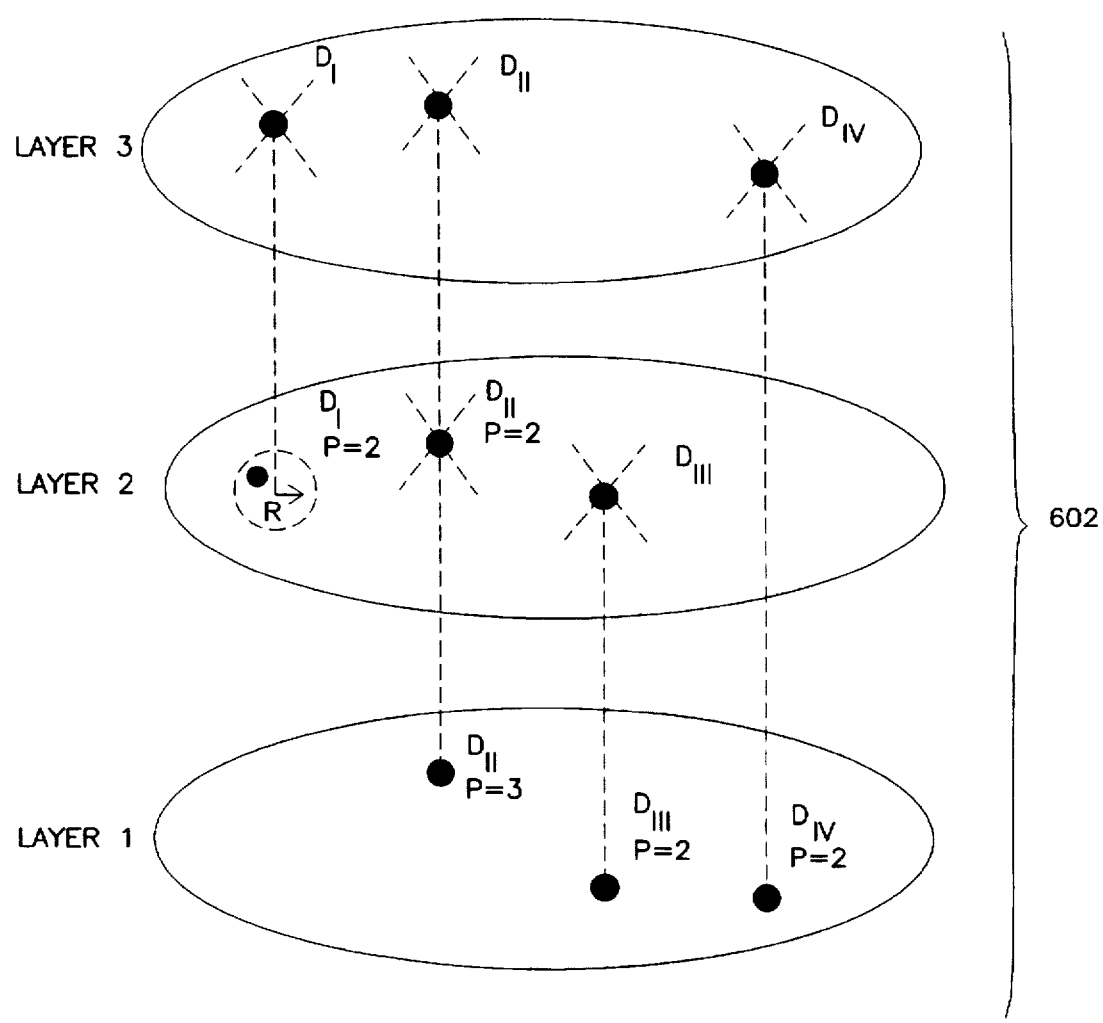
FIG. 6b is a schematic illustration of semiconductor wafer layers upon which the layer stacking functions of FIG. 6a are performed.

FIG. 6b is a schematic illustration of a semiconductor wafer 602 having multiple layers with defects (D) thereon. Three of such layers (Layer 1, Layer 2 and Layer 3) are shown, to illustrate, in conjunction with FIG. 6a, the stacking functions of step 406.

Referring to FIGS. 6a and 6b, the defect stacking functions of step 406 are performed in order to determine: (1) the layer of first occurrence of each defect (D) on the wafer 602; and (2) the number of times the same defect (D) is caught on different layers. The result of the stacking functions is a stack map of a wafer that includes, for each layer, defect parameter information pertaining to defect type, defect size, layer of first occurrence and number of times a defect is caught, i.e., its redetect count.

In step 604 a processing loop begins that, as explained below, is executed for each fabrication layer of the wafer 602, beginning with the last applied layer, which in the present example is Layer 3 shown in FIG. 6b. The processing loop of steps 604–630, when performed for all indicated layers of the wafer 602, indicates the level of first occurrence of each of the defects (D) on the wafer and also indicates a redetect parameter (P) that specifies the number of layers upon which the same defect is caught. The redetect parameter (P) is useful because if the same defect is detected on multiple layers, it is likely a very large, or penetrating, defect and such information can impact the die kill factor that should be assigned for that defect.

Steps 606–624 define a processing loop performed for each defect on the current layer being examined. Steps 608–618 define a processing loop performed for each layer previous to the current layer being examined.

Thus in step 604 execution begins with the last layer of the wafer and the loop of steps 604–630 is performed for every layer. Step 606 begins for each detected defect on the current layer being examined and the loop of steps 606–624 is performed for every defect on the current layer. Step 608 begins for the previous layer to the current layer being examined, and the loop of steps 608–618 is performed for every previous layer.

In step 610, the program 22 looks for a defect on the previous layer to the current layer for a defect that is within a radius (R) of the defect on the current layer. In step 612 if no defect is found within radius (R), in step 614 a determination is made if there are more previous layers. If there are more previous layers in step 614, then execution returns to step 610 and the next previous layer is examined accordingly. If in step 614 there are no previous layers, execution proceeds to step 618.

In step 610 above, the radius (R) is set by experimentation. In one application, the value of R may be, for example, in a range of about 50 to 500 microns. The rules for determining R may also specify that R is fixed, unless the defect is determined to be part of a big cluster, whereupon a different radius (R) may be appropriate.

If in step 612 a defect is found within radius (R) on the previous layer, execution proceeds to step 615. In step 615 the current defect is denoted with a redetect parameter (P). In step 616 the current defect is deleted from the current level. This is because the defect found on the previous layer, being within radius (R), is really the same defect and the program is attempting to locate the level of first occurrence of such defect. In step 617 the redetect parameter (P) is incremented by one, thus indicating the number of times the defect has been detected.

In step 618 the processing loop begun in step 608 for each previous layer is completed. In step 620 a determination is made whether there are more defects in the current layer to be examined, and if so, in step 622 execution proceeds to the next defect on the current layer. Steps 608–620 are then repeated for that defect. Otherwise, in step 620, if there are no more defects, execution of the processing loop for each defect on the current layer, begun in step 606, ends in step 624.

In step 626 a determination is made if there are more previous layers upon which the processing loop of steps 604–630 are to be performed. If so, in step 628 execution proceeds to the next previous layer. Otherwise, execution of the loop for each layer begun in step 604 ends in step 630.

Referring to FIG. 6b, operation of the layer stacking functions just described is exemplified. Beginning with Layer 3 (step 604) as the current layer, which is the last applied in time during fabrication, a first defect $D_I$ is identified (step 606). Subsequently, and beginning with the previous Layer 2 (step 608), the program looks for any defects that are within a radius (R) of $D_I$ (step 610). As shown in FIG. 6b, a defect $D_I$ exists within the radius (R). Defect $D_I$ in Layer 3 is denoted with a redetect parameter (P) (step 615). Defect $D_I$ in Layer 3 is deleted from Layer 3 (step 616). The redetect parameter (P) is incremented by one, i.e., P=2 (step 617). Execution proceeds to identify another defect $D_{II}$ on the current Layer 3 (steps 620, 622). The process loop of steps 608–618 is repeated for defect $D_{II}$, wherein the defect $D_{II}$ gets deleted from Layer 3 and the redetect parameter P gets incremented so that P=2, on Layer 2. The process loop of steps 608–618 is again repeated for defect $D_{III}$, wherein the defect $D_{III}$ gets deleted from Layer 3 and the redetect parameter P gets incremented so that P=2 on Layer 1.

The process loop of steps 604–630 is repeated for Layers 2 and 3, so that it is determined that for $D_I$, the layer of first occurrence is Layer 2 and the redetect parameter P=2 indicates $D_I$ was detected twice. For $D_{II}$, the layer of first occurrence is determined to be Layer 1 and the redetect parameter P=3 indicates $D_{II}$ was detected three times. For $D_{III}$, the layer of first occurrence is determined to be Layer 1 and the redetect parameter P=2 indicates $D_{III}$ was detected twice. For $D_{IV}$, the layer of first occurrence is determined to be Layer 1 and the redetect parameter P=2 indicates $D_{IV}$ was detected twice.

Table II below specifies the syntax of the rule descriptions used to assign the kill factors to each defect on each wafer, as required by step 408 of FIG. 4 for the yield predict program 22.

TABLE II

Kill Factor Rules
Rules (1-m) for a Specific Layer:

| Descriptions (Defect Type, \|Size\|) | Kill Factors (Single, Multi) |
|---|---|
| Rule 1: $T^1_1, T^1_2, \ldots$ $T^1_n$ [$S^1_{min}, S^1_{max}$] $K^1_{single}$ | $K^1_{multi}$ |
| Rule 2: $T^2_1, T^2_2, \ldots$ $T^2_n$ [$S^2_{min}, S^2_{max}$] $K^2_{single}$ | $K^2_{multi}$ |
| . | . |
| . | . |
| . | . |
| Rule m: $T^m_1, T^m_2, \ldots$ $T^m_n$ [$S^m_{min}, S^m_{max}$] | $K^m_{single}, K^m_{multi}$ |

In Table II it is illustrated that a number (up to m) of rules may be generated for each layer of a wafer, whereupon a particular kill factor (K) value is assigned to defects in that layer that match certain defect type ($T_1 \ldots T_n$), T), defect size and redetect count (P) parameters. A different kill factor ($K_{single}$ or $K_{multi}$) is specified for each rule depending upon the redetect count (P) associated with that defect. For example, if a defect is detected only once (P=1), it has a kill factor ($K_{single}$) while if it is a defect that was detected multiple times (P=2 or more) it has a kill factor ($K_{multi}$).

The rule descriptions (type (T) and size (S)) are specified with the aid of initialization parameters wherein the defect types are replaced with classification codes (an integer from 0 to 255) or by negative one, where negative one applies to all remaining defect types not enumerated. A rule description may have one or more classification codes specified. The size ranges [Smin, Smax] are expressed as real numbers.

The rule descriptions for each layer are specified with the aid of initialization parameters defined in an initialization file.

The rule descriptions, along with the kill factors assigned to each rule description, are stored in the initialization file for access by the program 22 in performing its kill factor assignment and die loss calculation (i.e., yield predict) functions, described further below.

Having defined the rule descriptions, the appropriate kill factors ($K_{single}$ and $K_{multi}$) can be assigned to each rule description in a number of ways. The kill factors can be assigned manually or automatically, for example.

Kill factors may be assigned manually to the rule descriptions wherein defects on the wafer layers are examined by an operator who makes a determination whether the defect is a killer or not. If a defect is a killer, it is assigned a value of 1 and all others (i.e., not killers) are assigned a value of 0. For a particular rule description, then, the 1's and 0's are added together and divided by their total to compute an average, which will be a real number between 0 and 1. This average number is the kill factor (K) for that rule description.

Alternatively, kill factors may be assigned automatically to the rule descriptions by comparison of the scanned defects of the stack map (FIG. 6b) generated in step 406 of FIG. 4, to a test bit map of actual wafer failures. Specifically, during manufacturing wafers are tested to identify critical electrical circuit failures. The failures, considered killer defects, are then compared using a module of the program 22 to the scanned defects of the stackmap. Those defects of the stack map that correspond to the bit map failures are designated as killers. The killers are assigned a value of 1 and non-killers are assigned a value of 0, whereupon for each rule description the 1's and 0's are averaged to compute the kill factor.

Figure 7B:
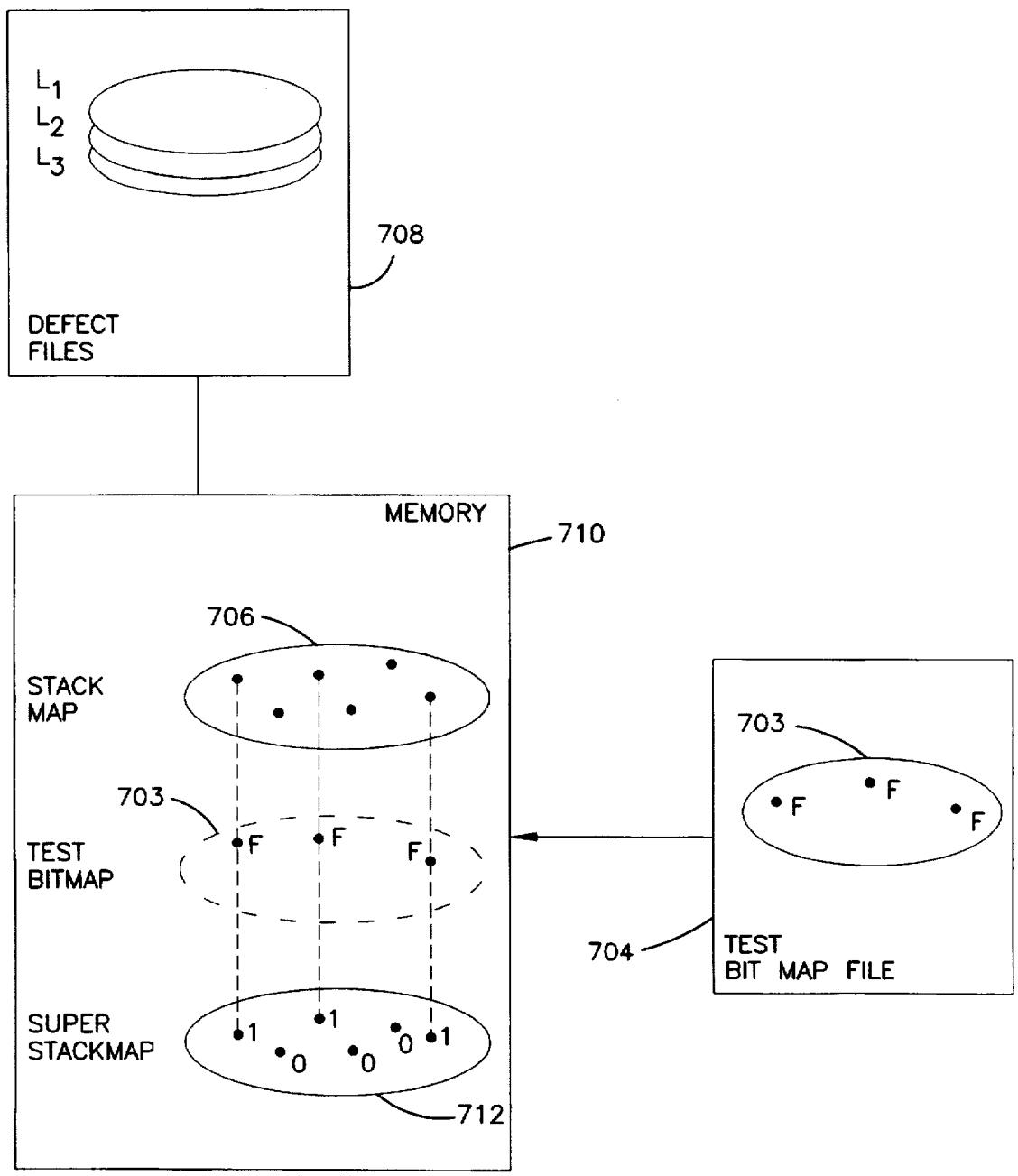

FIGS. 7a and 7b describe a module of the yield predict program 22 used to assign kill factors to defects, as referred to previously in step 408 of FIG. 4. FIG. 7a is a process flow diagram 700 of the kill factor assignment functions while FIG. 7b is a schematic illustrating the comparison of the stack map (FIG. 6b) generated by the program 22 to a test bit map of known failures (F) produced from a wafer test machine (not shown).

In step 702, the program 22 reads a test bit map 703 (FIG. 7b) of electrical failures (F) obtained from a semiconductor wafer produced on the line 12 and subsequently tested (as shown in block 30 of FIG. 1), using conventional test equipment (not shown). The test bit map 703 is stored in a test bit map file 704 for access by the program 22. In step 705 the program 22 reads the stack map 706 of defect parameters corresponding to the scanned wafer defects, it being understood the stack map is that described previously with respect to FIGS. 6a and 6b, corresponding to step 406 of FIG. 4. It is further understood the stack map 706 is generated by the program 22 as described previously using input from defect files 708 pertaining to individual defect layers (e.g., L_1, L_2, L_3), such as KLA Results Files produced by a scan tool 14 (FIG. 1).

In step 709 the kill factor rule descriptions from an initialization file are read, it being understood that the kill factor rule descriptions are those previously described with reference to Table II. As mentioned previously, the rule descriptions specify defect type, defect size, layer of first occurrence and redetect count.

The stack map 706 and the test bit map 703 form structures in a memory 710 of the computer on which the program 22 is operating, such as the computer 48 (FIG. 1). In step 711 the stack map 706 and the test bit map 703 are compared to generate a super stack map 712. The super stack map 712 has all of the same defect parameter information as the stack map 712, but it also includes indications of which defects of the stack map (i.e., scanned defects) correspond to electrical circuit failures (F) determined from actual testing of wafers. On the super stack map 712, the scanned defects that caused electrical failures (F) are assigned a bit value of 1 while scanned defects that did not cause electrical failures are assigned a bit value of 0.

In step 713, for each rule description a process is performed to assign the appropriate kill factor to it. Specifically, the bit values (i.e., 0's and 1's) of defects meeting a rule description are added together and averaged to produce a real number between 0 and 1. This number is the kill factor for that rule description. Referring to Table II, the kill factor (K) is then placed in the table for that rule. It is understood that where the redetect count for defects is greater than 1, a separate rule description exists that otherwise is the same but contemplates a multiple redetect count, whereupon a different kill factor (i.e., $K_{multi}$) is assigned to it.

Once the kill factors are assigned to all of the rule descriptions, the kill factors for each rule are written back to the initialization file. The rule descriptions, as described in the Table II, are thus updated with completed kill factors filled in.

In this manner, kill factors are assigned to each scanned defect on the wafer. To determine what the kill factor is for any given defect on the wafer, the defect is matched to the rule that contains the corresponding defect parameters. Upon finding the rule with the same defect parameters (i.e., layer of first occurrence, type, size, redetect count) the kill factor is therein expressed for that rule.

It is understood the process of assigning kill factors to the rule descriptions may be performed at any time, whereupon the kill factors can be updated based upon changes occurring in the manufacturing process that result in the generation of new test bit map files 704. It is envisioned that the program 22 can be instructed at any time to update the kill factors assigned to the rule tables, by receiving input data in the form of new test bit map files 704. The new test bit map files 704 are constructed from tests performed at the end of the fabrication process. Accordingly, the kill factors can be adjusted based upon new test file results in order to improve the yield prediction or to encompass new process changes.

Referring again to FIG. 4, once the kill factors are assigned to each defect on the wafer in the form of the rule descriptions of Table II in step 410, execution proceeds to steps 412, 414, and 416 wherein the kill factor information is utilized for yield prediction calculations.

In step 412 the net failure probability (P) for each wafer die is computed. Specifically, for each die (i) on the wafer, the failure probability ($P_i$) is computed by the formula of equation (1) below:

$$P_i = 1 - \pi_{jtk} (1 - K_{ijtk}) \tag{1}$$

where i is the die number; j is the layer number; t is the defect type; and k is the defect number within a die i at a layer j of type t.

The Probability of failure of die i due to layer j from defects of type t is computed by the formula of equation (2) below:

$$P_{ijt} = P_i \frac{\sum_k P_{ijtk}}{\sum_{jtk} P_{ijtk}} \tag{2}$$

The total loss on the wafer from all levels and defect types ($DL_T$) is computed by the equation (3) below:

$$DL_T = \sum_i P_i \tag{3}$$

The total loss due to layer j and type t ($L_{jT}$) is computed by equation (4) below:

$$L_{jt} = \sum_i P_{ijt} \tag{4}$$

The total loss due to layer j and all types (LJ) is computed by equation (5) below:

$$L_j = \sum_t L_{jt} \tag{5}$$

FIG. 8 is an example of an output format for die loss summaries expressed in the form of a table. The die loss output format is generated by the program 22 as an ASCII file with a horizontal header line for each lot followed by a horizontal line for each layer. The header line explains the information contained in each vertical column for each layer. The vertical columns pertain to lot number, wafer number, step identification, total die loss for individual layers and all defect types, and total die loss for individual layers and particular defect types (e.g., type 0, type 1, type 4).

The values in the column for total die loss for all layers can be added together to provide the estimated total die loss on the wafer from all levels and defect types. The present example illustrates the die loss output format for a lot with four layers and three defect classifications (types 0, 1, 4) exist. It is understood that more elaborate outputs are possible depending upon the lot, wafer, and defect criteria involved.

Figure 9:
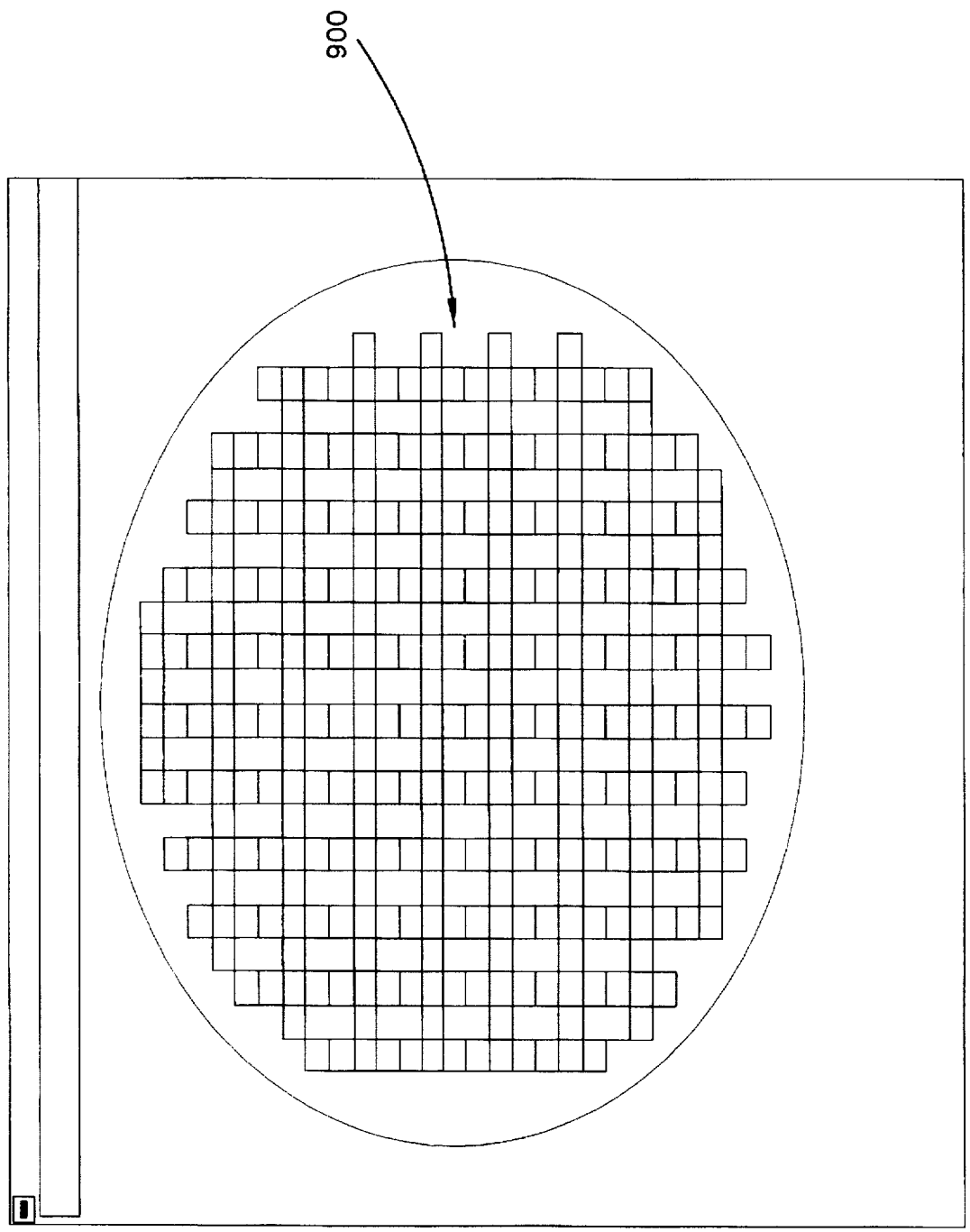
FIG. 9 illustrates example wafer maps of die loss information generated by the system of FIG. 1.

FIG. 9 illustrates an example wafer map 900 generated according to step 414 of FIG. 4. The wafer map 900 shows locations of defects causing die to have non-zero probabilities of failure.

It is understood that the present invention can take many forms and embodiments. The embodiments shown herein are intended to illustrate rather than to limit the invention, it being appreciated that variations may be made without departing from the spirit of the scope of the invention. For example, the preclassify and yield predict programs may be organized into any number of different modules or computer programs for operation on either or both of the system 16 and the tool 14. The computer of the system 16 may not be required if the same functions are implemented on the scan tool computer. The programs may be used to classify types of codes other than those mentioned in the preferred embodiment. The techniques of the present invention may also apply to analyses other than those of the preferred embodiment. The programs may be implemented in any appropriate programming language and run in cooperation with any computer system or scan tool. The review process described herein may be performed manually or by machine vision recognition of defect attributes.

Although illustrative embodiments of the invention have been shown and described, a wide range of modification, change and substitution is intended in the foregoing disclosure and in some instances some features of the present invention may be employed without a corresponding use of the other features. Accordingly, it is appropriate that the appended claims be construed broadly and in a manner consistent with the scope of the invention.

What is claimed is:

1. A computer program for analyzing data associated with defects on a substrate, the substrate including multiple layers and multiple die, the computer program stored on a computer-readable medium, comprising:

instructions for reading files containing defect data for selected layers of said substrate, said defect data including defect type and defect size information;

instructions for stacking said defect data to identify a layer of first occurrence of each defect and a count of layers upon which each defect is redetected, said defect data pertaining to occurrences on layers other than said layer of first occurrence being discarded;

instructions for assigning a kill factor to each defect that remains after stacking, according to a set of rules, each said rule specifying defect parameters that include layer of first occurrence, redetect count, defect size, and defect type; and instructions for determining failure probabilities of the die according to kill factors assigned to said defects.

2. The computer program of claim 1 further comprising instructions for determining from failure probabilities of the die, an estimated total die loss for said substrate.

3. The computer program of claim 1 further comprising instructions for determining from failure probabilities of the die, an estimated die loss for selected layers of said substrate.

4. The computer program of claim 1 further comprising instructions for determining from failure probabilities of the die, an estimated die loss for selected defect types of substrate.

5. The computer program of claim 1 wherein said instructions for assigning a kill factor include reading data generated by manual identification of killer defects.

6. The computer program of claim 1 wherein said instructions for assigning a kill factor include instructions for comparing said defect data resulting from stacking to test bit map data.

7. The computer program of claim 1 wherein said instructions for assigning a kill factor comprises instructions for:

comparing said defect data resulting from stacking to test bit map data to generate a map of data indicating which defects caused electrical failures and which defects did not cause electrical failures;

assigning a bit value of 1 to defects that caused electrical failures and assigning a bit value of 0 to defects that did not cause electrical failures; and for each rule, identifying defects having defect data that satisfy said rule, determining an average of bit values of identified defects, and establishing said average as said kill factor for said rule.

8. The computer program of claim 1 further comprising instructions for generating from failure probabilities of the die, a table indicating estimated die loss of selected layers of said substrate and estimated die loss for selected defect types of said substrate.

9. The computer program of claim 1 further comprising instructions for generating from failure probabilities of the die, substrate maps indicating estimated die loss for selected layers of said substrate.

10. The computer program of claim 1 further comprising instructions for generating warnings when failure probabilities of the die exceed predetermined limits.

11. A method for analyzing data associated with defects on a substrate, the substrate including multiple layers and multiple die, comprising the steps of:

reading files containing defect data for selected layers of said substrate, said defect data including defect type and defect size information;

stacking said defect data to identify a layer of first occurrence of each defect and a count of layers upon which each defect is redetected, said defect data pertaining to occurrences on layers other than said layer of first occurrence being discarded;

assigning a kill factor to each defect that remains after stacking, according to a set of rules, each said rule specifying defect parameters that include layer of first occurrence, redetect count, defect size, and defect type; and determining failure probabilities of the die according to kill factors assigned to said defects.

12. The method of claim 11 further comprising the step of determining from failure probabilities of the die, an estimated total die loss for said substrate.

13. The method of claim 11 further comprising the step determining from failure probabilities of the die, an estimated die loss for selected layers of said substrate.

14. The method of claim 11 further comprising the step of determining from failure probabilities of the die, an estimated die loss for selected defect types of said substrate.

15. The method of claim 11 wherein said step of assigning a kill factor includes the step of manually identifying killer defects.

16. The method of claim 11 wherein said step of assigning a kill factor includes the step of comparing said defect data from said stacking step to test bit map data.

17. The method of claim 11 wherein said assigning step includes the steps of:

comparing said defect data resulting from stacking to test bit map data to generate a map of data indicating which defects caused electrical failures and which defects did not cause electrical failures;

assigning a bit value of 1 to defects that caused electrical failures and assigning a bit value of 0 to defects that did not cause electrical failures; and for each rule, identifying defects having defect data that satisfy said rule, determining an average of bit values of identified defects, and establishing said average as said kill factor for said rule.

18. The method of claim 11 further comprising the step of generating from failure probabilities of the die, a table indicating estimated die loss for selected layers of said substrate and an estimated die loss for selected defect types of substrate.

19. The method of claim 11 further comprising the step of generating from failure probabilities of the die, substrate maps indicating an estimated die loss for selected layers of said substrate.

20. The method of claim 11 further comprising the step of generating warnings when failure probabilities of the die exceed predetermined limits.

21. A computer program for analyzing data associated with defects on a substrate, the substrate including multiple layers and multiple die, the computer program stored on a computer-readable medium, comprising:
- instructions for reading files containing defect data for selected layers of said substrate, said defect data including defect type and defect size information;
- instructions for estimating, from said defect data, defect type codes for unclassified ones of said defects on said substrate, extrapolated from classified ones of said defects on said substrate;
- instructions for stacking said defect data to identify a layer of first occurrence of each defect and a count of layers upon which each defect is redetected, said defect data pertaining to occurrences on layers other than said layer of first occurrence being discarded;
- instructions for assigning a kill factor to each that remains after stacking, according to a set of rules, each said rule specifying defect parameters that include layer of first occurrence, redetect count, defect size, and defect type;
- instructions for determining failure probabilities of the die according to kill factors assigned to said defects; and
- instructions for determining from said failure probabilities the estimated die loss for said substrate.

22. The computer program of claim 21 further comprising instructions for determining from failure probabilities of the die, an estimated die loss for selected layers of said substrate.

23. The computer program of claim 21 further comprising instructions for determining from failure probabilities of the die, an estimated die loss for selected defect types of substrate.

24. The computer program of claim 21 wherein said instructions for assigning include, instructions for:
- comparing said defect data resulting from stacking to test bit map data to generate a map of data indicating which defects caused electrical failures and which defects did not cause electrical failures;
- assigning a bit value of 1 to defects that caused electrical failures and assigning a bit value of 0 to defects that did not cause electrical failures; and for each rule, identifying defects that satisfy said rule, determining an average of bit values of identified defects, and establishing said average as said kill factor for said rule.

25. The computer program of claim 21 further comprising instructions for generating from failure probabilities of the die, a table indicating estimated die loss for selected layers of said substrate and a estimated die loss for selected defect types of substrate.

26. The computer program of claim 21 further comprising instructions for generating from failure probabilities of the die, substrate maps indicating an estimated die loss for selected layers of said substrate.

27. The computer program of claim 21 further comprising instructions for generating warnings when failure probabilities of the die exceed predetermined limits.

* * * * *

UNITED STATES PATENT AND TRADEMARK OFFICE
CERTIFICATE OF CORRECTION

PATENT NO. : 5,777,901
DATED : July 7, 1998
INVENTOR(S) : Berezin et al.

It is certified that error appears in the above-identified patent and that said Letters Patent is hereby corrected as shown below:

Col. 13, line 23: "$N_r$" should read --$N_t$--.

In The Claims:

Col. 20, line 31: Insert the word "of" after --step--.

Col. 21, line 17: Insert the word "defect" after --each--.

Col. 22, line 18: Insert the word "an" after --indicating--.

Col. 22, line 19: "a" should be --an--.

Signed and Sealed this

Twenty-second Day of June, 1999

Attest:

Attesting Officer

Q. TODD DICKINSON

Acting Commissioner of Patents and Trademarks